(12) United States Patent
Hakamata

(10) Patent No.: US 8,665,444 B2
(45) Date of Patent: Mar. 4, 2014

(54) OPTICAL MEMBER AND SURFACE PLASMON RESONANCE MEASURING APPARATUS

(75) Inventor: Masashi Hakamata, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 370 days.

(21) Appl. No.: 13/076,368

(22) Filed: Mar. 30, 2011

(65) Prior Publication Data

US 2011/0242541 A1    Oct. 6, 2011

(30) Foreign Application Priority Data

Mar. 31, 2010    (JP) ................................ 2010-084608

(51) Int. Cl.
*G01N 21/55*    (2006.01)
(52) U.S. Cl.
USPC ........................................................... 356/445
(58) Field of Classification Search
USPC .................... 356/445–448, 450–458
See application file for complete search history.

(56) References Cited

U.S. PATENT DOCUMENTS

| | | | | |
|---|---|---|---|---|
| 3,442,571 A * | 5/1969 | Itzkan | ...................... | 359/489.09 |
| 4,525,034 A * | 6/1985 | Simmons | .................. | 359/485.02 |
| 6,507,402 B2 * | 1/2003 | Negami et al. | ................ | 356/445 |
| 7,454,111 B2 * | 11/2008 | Shiba et al. | .................... | 385/131 |
| 7,791,730 B2 * | 9/2010 | Lee et al. | ....................... | 356/445 |
| 2004/0047770 A1 | 3/2004 | Schawaller et al. | | |
| 2007/0003183 A1 | 1/2007 | Shiba et al. | | |
| 2009/0218499 A1 | 9/2009 | Kimura | | |
| 2010/0047820 A1 | 2/2010 | Ohtsuka | | |
| 2010/0092996 A1 | 4/2010 | Verschuren et al. | | |

FOREIGN PATENT DOCUMENTS

| | | |
|---|---|---|
| EP | 0 851 230 A1 | 7/1998 |
| JP | 2002-328087 A | 11/2002 |
| JP | 2004-163402 A | 6/2004 |
| JP | 2006-112808 A | 4/2006 |
| JP | 2010-48756 A | 3/2010 |
| WO | WO 2008/072156 A2 | 6/2008 |

OTHER PUBLICATIONS

Extended European Search Report dated Jul. 25, 2011.
Notice of Grounds for Rejection dated Jun. 11, 2013, with English translation.

* cited by examiner

*Primary Examiner* — Gregory J Toatley, Jr.
*Assistant Examiner* — Jarreas C Underwood
(74) *Attorney, Agent, or Firm* — McGinn Intellectual Property Law Group, PLLC

(57) ABSTRACT

The shape of a prism is set such that an excitation light beam that enters the prism to cause surface plasmon resonance to be generated is not irradiated onto the corners of the prism after being totally reflected within the prism. The angle of a surface that the excitation light exits the prism is set to an angle at which the excitation light beam is not totally reflected. Thereby, the excitation light beam returning to a light source, and being scattered within the prism are prevented, and therefore the accuracy of measurements can be improved.

7 Claims, 12 Drawing Sheets

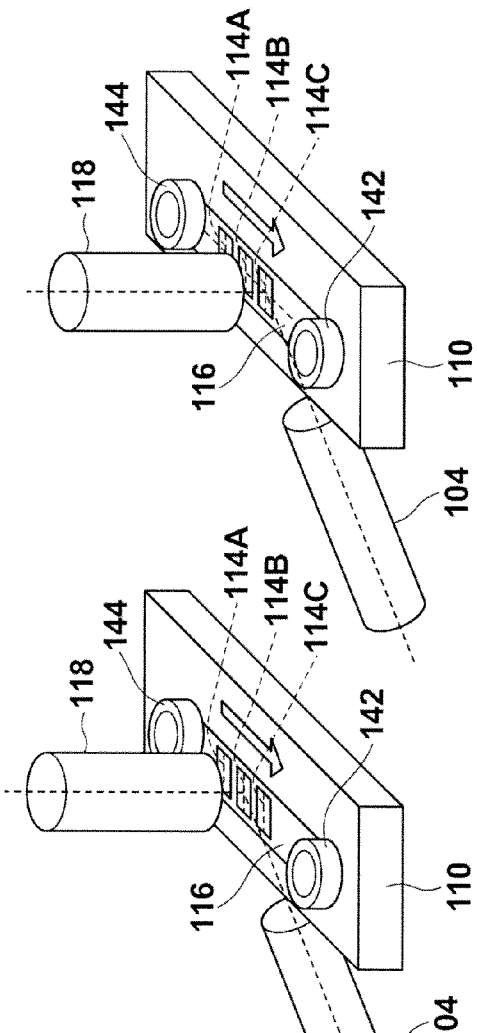

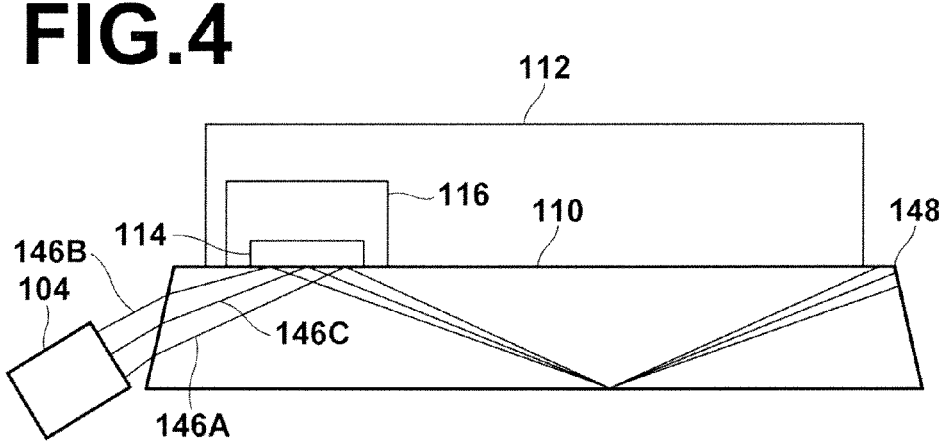
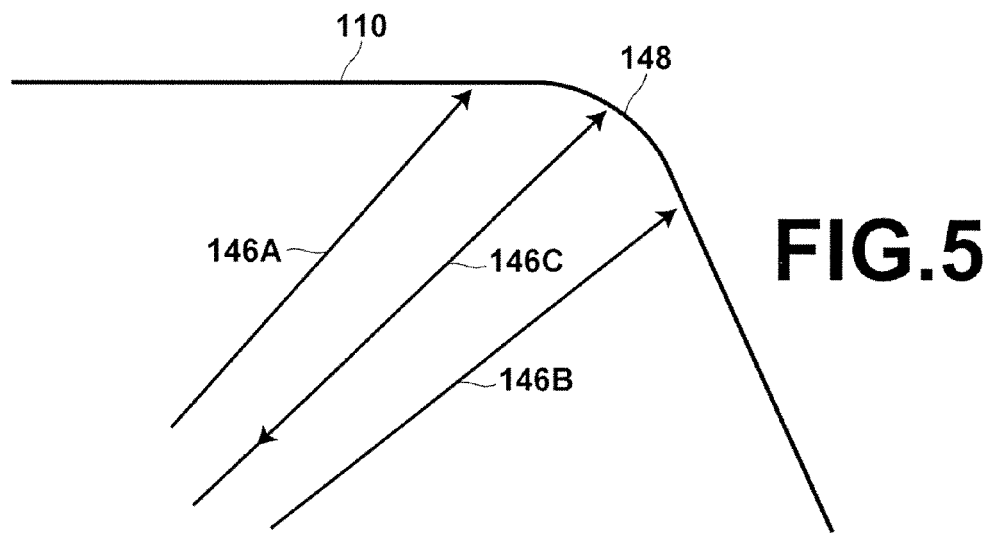

OPTICAL MEMBER AND SURFACE PLASMON RESONANCE MEASURING APPARATUS

BACKGROUND OF THE INVENTION

1. Field of the Invention

The present invention is related to an optical member. Particularly, the present invention is related to an optical member for use in a surface plasmon resonance measuring apparatus.

2. Description of the Related Art

Plasmon sensors that utilize the principles of the surface plasmon resonance phenomenon using evanescent waves to quantitatively analyze substances within samples are known. U.S. Patent Application Publication No. 20090218499 discloses an apparatus, in which a metal film is provided on a prism. A target substance labeled with a fluorescent substance is caused to bind onto the metal film, and a light beam is caused to enter the interface between the prism and the metal film at an angle that satisfies conditions for plasmon resonance, to generate a strong electric field is generated on the metal film. The fluorescent substance is strongly excited by the electric field, and the fluorescence generated thereby is measured.

It is necessary to cause an excitation light beam to be totally reflected at the interface between a prism and a metal film provided thereon, in order to cause surface plasmon resonance to occur in the vicinity of the metal film that functions as a sensor region. The prism is formed to have a cross sectional shape of an inverted triangle or a trapezoid. A light source emits a converged excitation light beam toward the prism such that the excitation light beam enters the prism through a side surface (also referred to as a light incident surface) and is totally reflected at the metal film. There are cases in which the excitation light beam is repeatedly totally reflected within the prism, and reaches a side surface (also referred to as a light output surface) opposite the light incident surface. In this type of apparatus, the excitation light beam is converged as it enters the prism and caused to be totally reflected at the sensor region at an area substantially the same as that of the metal film. Therefore, the excitation light beam converges then spreads as it propagated toward the light output surface after being totally reflected. In this case, if the excitation light beam is irradiated onto the corner formed by the upper surface of the prism and the light output surface, or onto the corner formed by the lower surface of the prism and the light output surface, components which are regularly reflected at the corner (hereinafter, referred to as returning light) propagate backwards along the optical path and enters the light source of the excitation light beam. If the returning light enters the light source, light emission by the light source is destabilized, and there are cases in which errors occur in the amount of detected fluorescence. In addition, if the excitation light beam is totally reflected at the light output surface of the prism, the excitation light beam is scattered within the prism, and there is a problem that the accuracy of measurement deteriorates. Providing a light shielding plate may be considered as a measure for preventing the returning light from entering the light source. However, because the returning light travels along the same optical path as the excitation light beam, the excitation light beam will also be shielded if the light shielding plate is provided. Adjusting the angle of the excitation light beam is another possible measure for preventing the returning light from entering the light source. However, adjustments to the angle of the excitation light beam are sensitive, and it is difficult for users to perform such adjustments when they utilize the plasmon sensors.

SUMMARY OF THE INVENTION

The present invention has been developed in view of the foregoing circumstances. It is an object of the present invention to provide an optical member that eliminates returning light, prevents total reflection of the excitation light beam at the light output surface, and improves the accuracy of measurement of a surface plasmon resonance measuring apparatus.

An optical member of the present invention is to be used in an apparatus that performs measurement of samples using an electric field generated by evanescent waves resonating with surface plasmon when an excitation light beam is totally reflected, the total reflection of the excitation light beam occurring within the optical member. The optical member is provided with a light output surface through which the excitation light beam is output. The angle of the light output surface with respect to the excitation light beam and the length of the optical member in the direction that the excitation light been propagates while being totally reflected are set such that the excitation light beam is not irradiated onto the corners of the optical member.

A configuration may be adopted, wherein the angle of the light output surface is set such that the angle of the excitation light beam with respect to the light output surface is smaller than an angle at which the excitation light beam is totally reflected.

The present invention provides an optical member that eliminates returning light. Therefore, a surface plasmon resonance measuring apparatus having improved accuracy of measurement can be provided.

BRIEF DESCRIPTION OF THE DRAWINGS

FIGS. 3A, 3B, and 3C are diagrams that illustrate a measuring operation performed by the surface plasmon resonance measuring apparatus of FIG. 1, wherein FIG. 3A illustrates a position which is measured first, FIG. 3B illustrates a position which is measured second, and FIG. 3C illustrates a position which is measured third.

FIG. 4 is a diagram that schematically illustrates the prism of the first embodiment and the manner in which an excitation light beam propagates through the interior of the prism.

FIG. 5 is a magnified view of a corner of the prism of the first embodiment.

DESCRIPTION OF THE PREFERRED EMBODIMENTS

Hereinafter, embodiments of the present invention will be described with reference to the attached drawings.

First Embodiment

Figure 1:
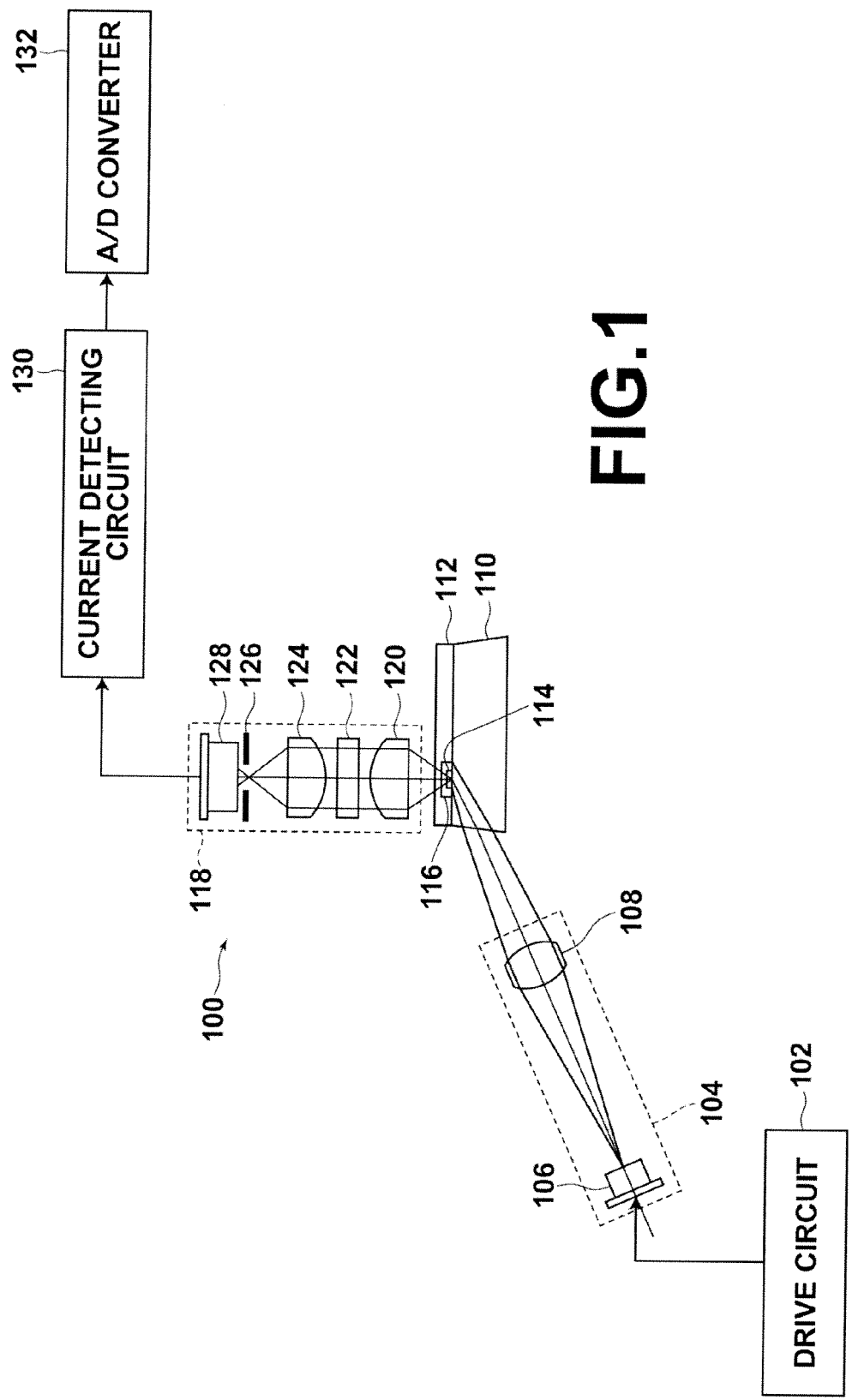
FIG. 1 is a diagram that schematically illustrates the configuration of a surface plasmon resonance measuring apparatus that employs a prism according to a first embodiment of the present invention.

FIG. 1 is a diagram that schematically illustrates the configuration of a surface plasmon resonance measuring apparatus 100 that employs a prism according to a first embodiment of the present invention. The configuration of the surface plasmon resonance measuring apparatus 100 will be described with reference to FIG. 1. The surface plasmon resonance measuring apparatus 100 is equipped with: a light source section 104; a drive circuit 102 for driving the light source section 104; a prism 110; a flow channel member 112; a light receiving section 118; a current detecting circuit 130; and an A/D converter 132. The light source section 104 includes a laser diode 106 and a lens 108. Metal films 114 are formed on the upper surface of the prism 110. In the present embodiment, the metal films 114 are gold films. The flow channel member 112 is provided on the upper surface of the prism 110, and forms a flow channel 116 around the metal film 114. The light receiving section 118 includes a lens 120, an excitation light cutoff filter, a lens 124, an aperture 126, and a photodiode 128. The light receiving section 118 having this configuration cuts off excitation light, and converts other light into electric charges. The current detecting circuit 130 detects charges generated at the light receiving section as electric currents. The A/D converter 132 converts the electric currents detected by the current detecting circuit 130 from analog signals to digital data.

Figure 2:
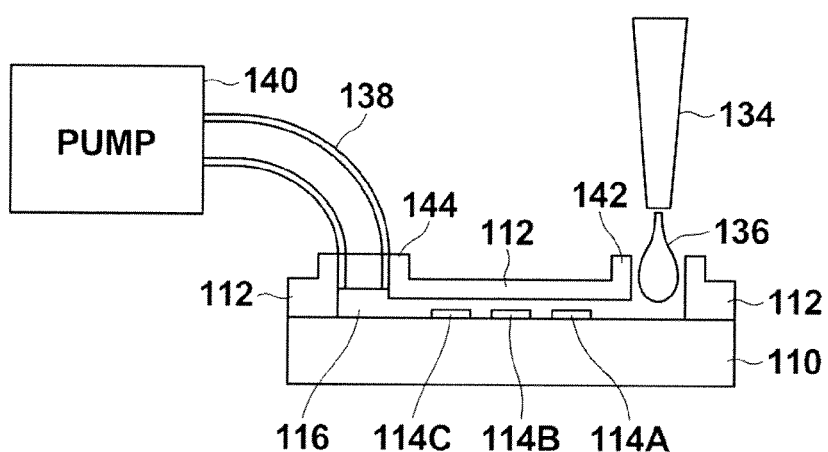
FIG. 2 is a view of the surface plasmon resonance apparatus of FIG. 1 from the right side in the drawing sheet of FIG. 1.

FIG. 2 is a view of the surface plasmon resonance apparatus of FIG. 1 from the right side in the drawing sheet of FIG. 1. FIG. 2 illustrates the prism 110 and the flow channel member 112 of FIG. 1, and the other components are omitted. The configuration of the prism 110 and the flow channel member 112 will be described in greater detail with reference to FIG. 2. Linearly arranged metal films 114A through 114C are formed on the upper surface of the prism 110. The flow channel member 112 is provided on the upper surface of the prism 110, and forms the flow channel 116 on the line along which the metal films 114A through 114C are arranged. Openings 142 and 144 are provided at the ends of the flow channel 116. A tube 138 is connected to the opening 144, and the tube 138 is connected to a pump 140. A pipette 134 is connected to the opening 142, and drips a sample 136 into the flow channel 116. The sample 136 passes over the metal films 114A through 114C by the pump 140 applying suction. Different processes are administered to the upper surfaces of each of the metal films 114A through 114C, and fluorescently labeled target substances which are present within the sample 136 are adsorbed onto the metal films 114A through 114C.

FIGS. 3A through 3C are diagrams that illustrate a measuring operation performed by the surface plasmon resonance measuring apparatus 100. Although not shown in the drawings, the sample 136 is continuously caused to flow through the flow channel 116 during the measuring operation. As illustrated in FIG. 3A, the light source section 104 emits a P polarized excitation light beam toward the lower surface of the metal film 114A through the prism 110 at an angle that satisfies conditions for plasmon resonance. When the excitation light beam is totally reflected at the metal film 114A, surface plasmon resonance occurs, and a strong electric field is generated on the metal film 114A. The fluorescent substance attached to the target substance is excited by the strong electric field, and generates fluorescence. The light receiving section 118 receives the fluorescence generated by the fluorescent substance, converts the light into electric charges, and outputs the electric charges. Then, the same process is performed with respect to the metal film 114B. Finally, the same process is performed with respect to the metal film 114C. The measurements illustrated in FIGS. 3A through 3C are repeated a predetermined number of times, and the detection target substances are quantified from data obtained by the measurements.

FIG. 4 is a diagram that schematically illustrates the prism 110 of FIG. 1 and the manner in which an excitation light beam propagates through the interior of the prism 110. The manner in which the excitation light propagates through the interior of the prism 110 will be described with reference to FIG. 4. In FIG. 4, line 146C denotes the central optical axis of the excitation light beam, and lines 146A and 146B denote the outline of the excitation light beam. That is, the excitation light beam is an angled light beam having a width from line 146A to 146B. The excitation light beam 146A~C emitted by the light source section 104 enters the prism 110, is totally reflected at the lower surface of a metal film 114, propagates through the prism 110 while being totally reflected by the upper and lower surfaces of the prism 110, and reaches a light output surface of the prism 110.

FIG. 5 is a magnified view of the vicinity of the light output surface of the prism 110. As illustrated in FIG. 5, a connecting portion 148 between the upper surface and the light output surface of the prism 110 is rounded when viewed microscopically, due to the limits of current molding techniques. The excitation light beam includes light having propagating directions of various angles. When the excitation light beam enters the rounded connecting portion 148, a portion thereof (146C in FIG. 5) propagates backward through the optical path that it had propagated through up to that point, and becomes returning light that reaches the light source section 104. In this manner, a portion of the excitation light beam that propagates through the prism 110 and reaches the connecting portion 148 becomes returning light. For this reason, the first embodiment sets the shape of the prism 110 such that an excitation light beam does not enter the corners thereof.

Figures 6A, 6B:
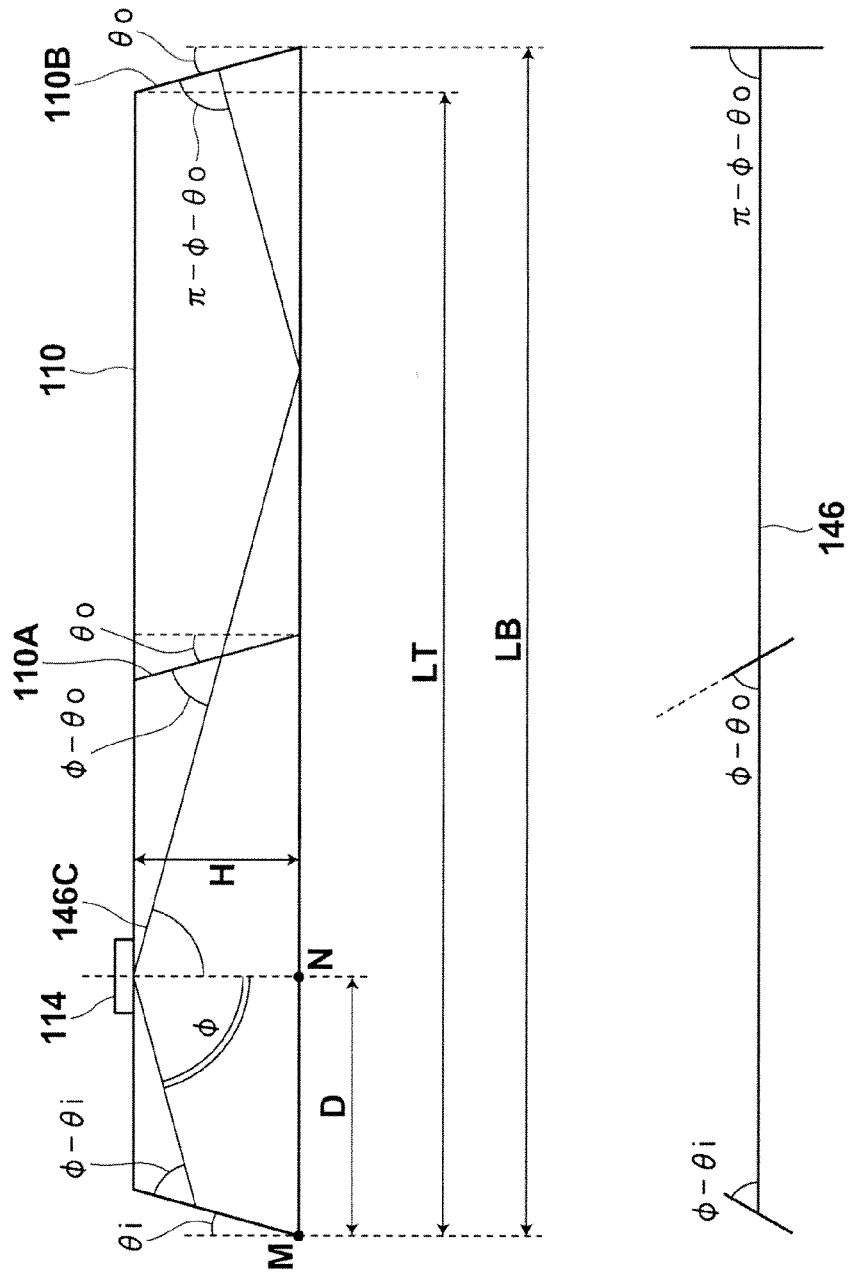
FIG. 6A is a diagram that illustrates the elements for setting the shape of the prism of the first embodiment.
FIG. 6B is a schematic diagram that illustrates the angle formed between linearly connected optical axes of a light beam which is totally reflected within the prism, and a light output surface.

FIG. 6A is a diagram that illustrates the elements for setting the shape of the prism of the first embodiment. Portions 146A and 146B of the excitation light beam are omitted from FIG. 6A. The cross section of the prism 110 is of a trapezoidal shape, having parallel upper and lower surfaces. Light output surfaces of the prism 110 are illustrated for a case in which a light output surface 110A is provided immediately after the excitation light beam is totally reflected at the metal film 114, and a case in which a light output surface 110B is provided immediately after the excitation light beam is totally reflected at the lower surface of the prism 110. Numerical values are set for $\phi$, $\theta i$, $\theta o$, D, LT, LB, and H as illustrated in FIG. 6A. In the state illustrated in FIG. 6A, $\theta i>0$ and $\theta o>0$. FIG. 6B is a schematic diagram that illustrates the angles formed between linearly connected optical axes of the excitation light beam 146C which is totally reflected within the prism, and the light output surfaces. The positions of the corners of the prism 110, that is, the values of LT and LB, are important in shaping the prism 110 such that an excitation beam is not irradiated onto the corners thereof.

Figure 7:
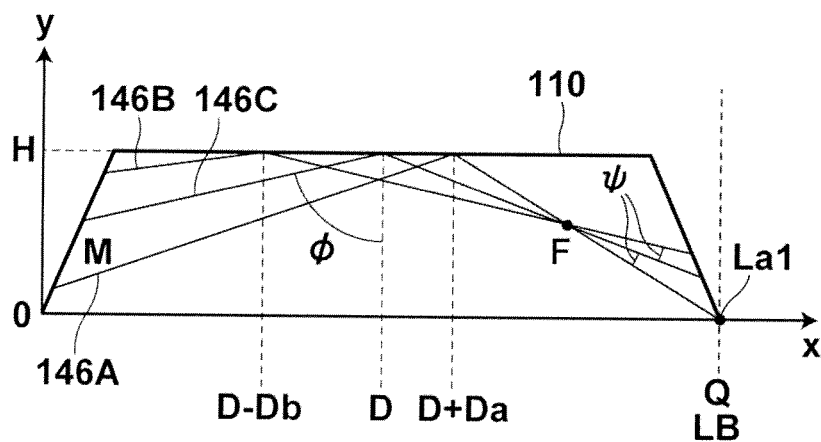
FIG. 7 is a diagram that illustrates a case in which a focal point exists within a prism, and an excitation light beam is reflected once within the prism.

Values of LT and LB that will not result in an excitation light beam being irradiated onto the corners of the prism 110 will be considered. First, a case in which an excitation is reflected once within the prism will be considered. FIG. 7 is a diagram that illustrates a case in which a focal point F exists within the prism 110, and an excitation light beam is reflected once within the prism. Only the central axis 146C of the excitation light beam was illustrated in FIG. 6A. However, lines 146A and 146B that represent the outline of the excitation light beam are also illustrated in FIG. 7. The angle formed between the outline 146A and the central axis 146 of the excitation light beam is designated as $\psi$. A coordinate system is set having point M as the origin, an x axis along the lower surface of the prism 110, and a y axis perpendicular to the x axis. The outline having a smaller y coordinate at the point where the excitation light beam 146A~146C enters the prism 110 is designated as 146A, and the outline having a greater y coordinate at the above point is designated as 146B. The x coordinate of the point at which the excitation light beam 146A contacts the upper surface of the prism is designated as D+Da, and the x coordinate of the point at which the excitation light beam 146B contacts the upper surface of the prism is designated as D−Db.

The excitation light beam 146A~146C that enters the prism 110 propagates in the x and y directions with an inclination which is determined by a surface plasmon resonance angle. The inclination of the excitation light beam 146A~446C in the propagating direction is inverted when the excitation light beam 146A~146C is totally reflected at the upper surface of the prism 110, and the magnitudes of the y coordinates of the excitation light beam 146A and the excitation light beam 146B are switched. The excitation light beam 146A~146C converges at focal point F after it propagates further. Beyond the focal point F, the y coordinate of the excitation light beam 146A~146C decreases while the outline thereof spreads. In this case, the corner of the prism 110 that the excitation light beam 146A~146C may be irradiated onto is the corner (LB, 0) formed by the light output surface and the lower surface of the prism 110. In this case, the entire excitation light beam will not be irradiated onto the corner (LB, 0) if the lower outline 146A of the excitation light beam is not irradiated onto the corner (LB, 0). That is, if LB is set such that the y coordinate of the excitation light beam 146A is 0 or greater, returning light will not be generated.

The shape of the prism 110 that would prevent the excitation light beam 146S from being irradiated onto the coiner (LB, 0) will be considered. If La1 is designated as a point (La1, 0) at which the excitation light beam 146A intersects with the x axis, the length LB of the bottom surface of the prism 110 must satisfy the condition LB<La1. The excitation light beam will not be irradiated onto the corner of the prism, and returning light can be prevented from being generated, by setting the length LB in this manner.

The x coordinate of La1 will be obtained in order to specifically set a length LB at which returning light will not be generated. A triangle formed by the broken line that indicates the position of D+Da, the lower surface of the prism 110, and the excitation light beam 146A will be considered. The angle at which the excitation light beam 146A enters the prism 110 is $\phi-\psi$. Accordingly, the angle at which the excitation light beam 146A is reflected by the prism 110 is also $\phi-\psi$. Therefore, the angle formed by the broken line that represents the position D+Da and the excitation light beam 146A is also $\phi-\psi$. In this case, the angle formed between the excitation light beam 146A and the bottom surface of the prism 110 is $(\pi/2)-(\phi-\psi)$. Therefore, La1 can be expressed by the following formula.

$$La1=[H/\tan\{(\pi/2)-(\phi-\psi)\}]-(D+Da)$$

H is the height of the prism, $\phi$ is an angle at which the excitation light beam is totally reflected, $\psi$ is an angle that represents the convergence of the excitation light, and D is the x coordinate at which the center of the excitation light beam is totally reflected at the metal film. $\Phi$ is a surface plasmon resonance angle which is determined in advance, and D is also predetermined with respect to $\phi$. H and $\psi$ may be determined by the designer of the apparatus. Accordingly, in the formula that represents La1, the unknown element is Da. That is, a value for LB that satisfies the condition LB<La1 can be determined by obtaining the value of Da. The value of Da is obtained by obtaining the x coordinate of the point at which the excitation light beam 146A is reflected by the upper surface of the prism.

Figure 8:
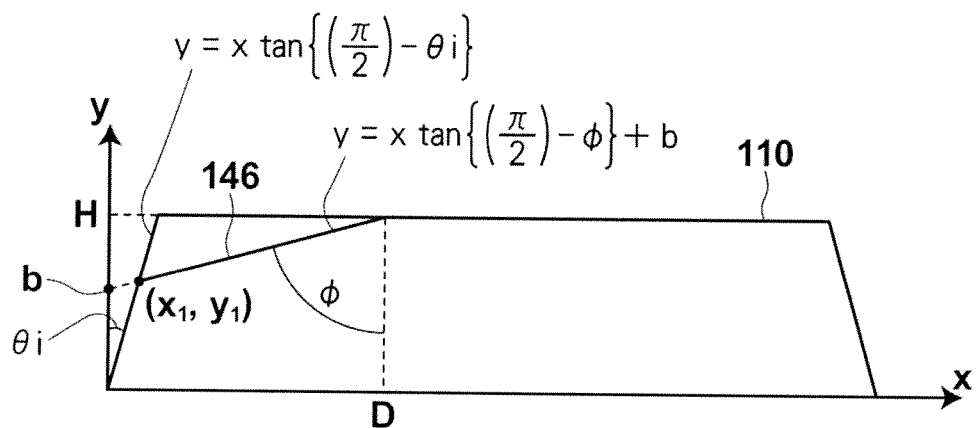
FIG. 8 is a diagram that illustrates a point at which an excitation light beam enters a prism.

First, the coordinates (x1, y1) of a point at which the excitation light beam enters the prism 110 are obtained, using FIG. 8, which employs the same coordinate system as that of FIG. 7. The point at which the excitation light beam 146 enters the prism 110 is determined as a single point, based on the surface plasmon resonance angle $\phi$ and the shape of the prism 110. If the angle formed by the light incident surface and the y axis is designated as $\phi i$, the light incident surface of the prism 110 will be a linear line segment expressed by the formula below.

$$y = x \cdot \tan\{(\pi/2) - \theta i\}$$

A line that represents the trajectory of the excitation light beam can be expressed by the formula below, employing the incident angle $\phi$ of the excitation light beam with respect to the upper surface of the prism 110.

$$y = x \cdot \tan\{(\pi/2) - \phi\} + b \text{ (}b\text{ is a constant)}$$

The point at which the excitation light beam enters the prism 110 is the intersection between the formula that represents the light incident surface of the prism 110 and the formula that represents the trajectory of the excitation light beam. The light incident surface of the prism and the excitation light beam 146 intersect at (x1, y1). Therefore, b can be expressed by the following formula by substituting x1 and y1 in the two formulas above, as shown in the formula below.

$$b = x1 \cdot \tan\{(\pi/2) - \theta i\} - x1 \cdot \tan\{(\pi/2) - \phi\}$$

A triangle formed by a line that represents the excitation light beam extended to the y axis, the upper surface of the prism 110 extended to the y axis, and the y axis will be considered. The length of the y axis within the triangle can be represented by the formula below.

$$H - b = H - x1[\tan\{(\pi/2) - \theta i\} - \tan\{(\pi/2) - \phi\}]$$

The angle formed between the upper surface of the prism 110 and the line that represents the excitation light beam is $\{(\pi/2) - \phi\}$. Therefore, the following formula holds true.

$$\tan\{(\pi/2) - \phi\} = H - x1[\tan\{(\pi/2) - \theta i\}] - \tan\{(\pi/2) - \phi\}]/D$$

The formula above may be organized and expressed as follows.

$$x1 = [H - D \cdot \tan\{(\pi/2) - \phi\}]/[\tan\{(\pi/2) - \theta i\} - \tan\{(\pi/2) - \phi\}]$$

Figure 9:
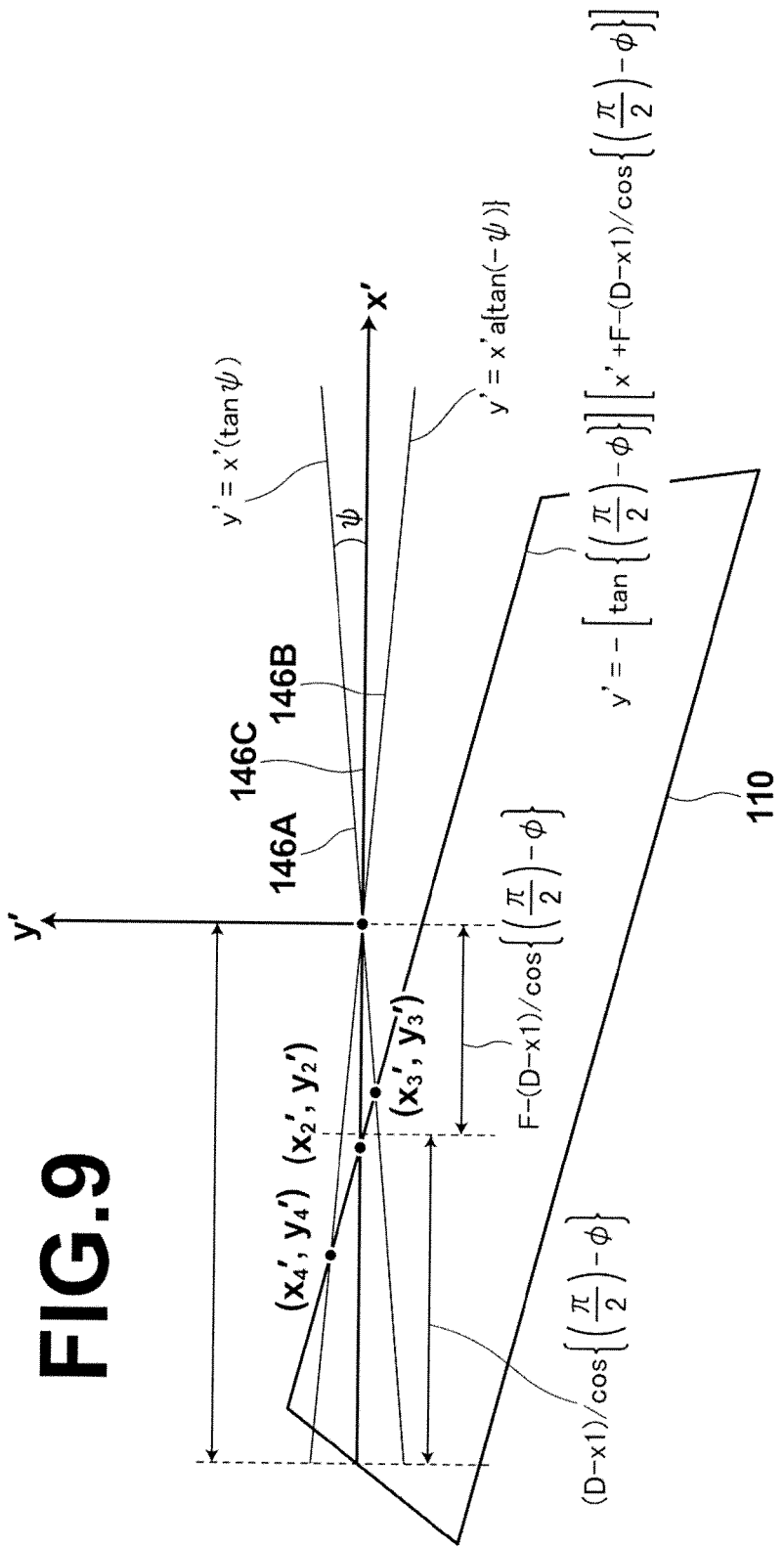
FIG. 9 is a diagram that illustrates a point at which an excitation light beam having a width intersects with the upper surface of a prism.

A case in which the excitation light beam is not totally reflected within the prism 110 and propagates linearly as illustrated in FIG. 9 will be considered. An x' axis is defined along the optical axis of an incident beam, with the position at which the excitation light beam converges as the origin. (x2', y2') are designated as the coordinates at which the excitation light beam 146C intersects with the upper surface of the prism 110. (x3', y3') are designated as the coordinates at which the excitation light beam 146A intersects with the upper surface of the prism 110. (x4', y4') are designated as the coordinates at which the excitation light beam 146B intersects with the upper surface of the prism 110. The formula that represents the line of the excitation light beam 146A is $y' = x' \cdot \tan \psi$, and the formula that represents the line of the excitation light beam 146B is $y' = x' \cdot \tan(-\psi)$. The point at which the excitation light beam 146C enters the prism 110 becomes (−F, 0). From the formulas derived from FIG. 8, x2' is expressed by the following formula.

$$x2' = F - (D - x1)/\cos\{(\pi/2) - \phi\}, y2' = 0$$

In addition, the angle formed between the prism 110 and the x' axis is $\{(\pi/2) - \phi\}$. Therefore, the upper surface of the prism is expressed by the formula below.

$$y' = -\tan\{(\pi/2) - \phi\}[x' + F - (D - x1)/\cos\{(\pi/2) - \phi\}]$$

x3' as derived from the formula that represents the prism 110 and the formula $y' = x' \cdot \tan \psi$ is expressed by the following formula.

$$x3' = -\tan\{(\pi/2) - \phi\}[F - (D - x1)/\cos\{(\pi/2) - \phi\}]/[\tan \psi + \tan\{(\pi/2) - \phi\}]; \text{ and}$$

$$y3' = \tan(\psi) \cdot \tan\{(\pi/2) - \phi\}[F - (D - x1)/\cos\{(\pi/2) - \phi\}/[\tan(\psi) + \tan\{(\pi/2) - \phi\}]$$

Employing the formulas above, Da can be expressed by the formula below.

$$Da = \sqrt{\{(x3' - x2')^2 + (y3' - y2')^2\}}$$

A value of Da calculated in this manner is substituted for La1 to calculate La1. By setting LB to be shorter than the calculated value of La1, returning light will not be generated in cases that the excitation light beam is reflected once within the prism and the focal point F is present within the prism 110.

Figure 10:
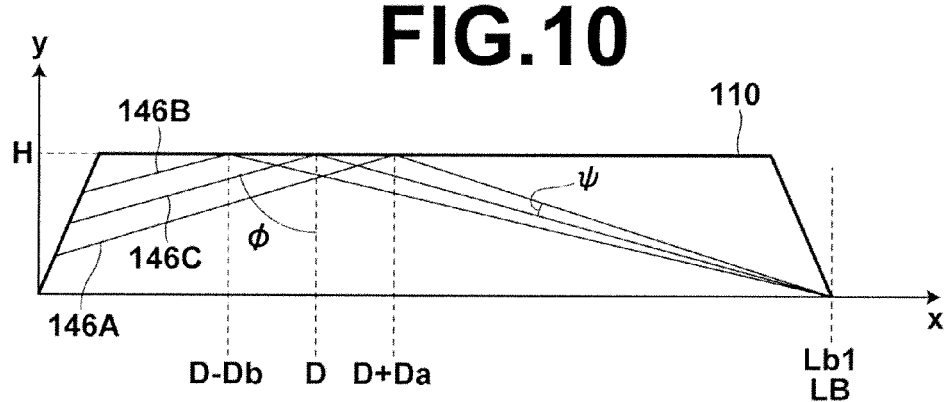
FIG. 10 is a diagram that illustrates a case in which a focal point exists outside a prism, and an excitation light beam is reflected once within the prism.

Next, a case will be considered, in which an excitation light beam is reflected once within the prism 110, and a focal point F exists toward the exterior of a light output surface of the prism 110, as in the example illustrated in FIG. 10. In this case, returning light will not be generated if the excitation light beam 146B is not irradiated onto the corner formed between the light output surface of the prism 110 and the lower surface of the prism 110. If a point at which the excitation light beam 146B intersects with a line extended from the lower surface of the prism 110 is designated as Lb1, LB<Lb1 becomes a necessary condition. Although a description of the calculations will be omitted, Lb1 is derived similarly to La1, and LB is set to be shorter than Lb1. Returning light will not be generated in cases that an excitation light beam is reflected once within the prism 110 and a focal point F exists toward the exterior of a light output surface of the prism 110, by setting LB in this manner.

Figure 11:
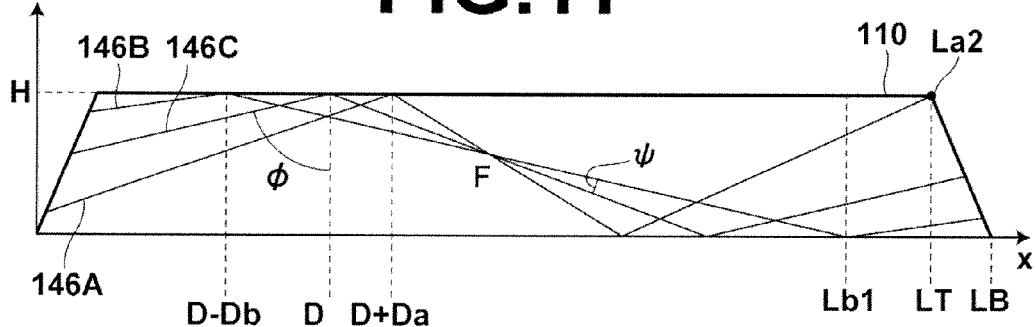
FIG. 11 is a diagram that illustrates a case in which an excitation light beam is reflected twice within a prism, and a focal point is positioned prior to the second reflection.

Next, a case will be considered, in which an excitation light beam is reflected twice within a prism, and a focal point is positioned prior to the second reflection, as illustrated in FIG. 11. In this case, it is necessary to consider both the angle formed between the upper surface and the light output surface of the prism 110, and the angle formed between the lower surface and the light output surface of the prism 110. If La2 is designated as the point at which the excitation light beam 146 totally reflected at the lower surface of the prism 110 intersects with the upper surface of the prism 110, La2 can be expressed by the following formula.

$$La2 = La1 + H/\tan\{(\pi/2) - (\phi - \psi)\}$$

The length LT of the upper surface the prism must satisfy the condition LT<La2. The excitation light beam will not be irradiated onto the corner formed by the upper surface and the light output surface the prism 110, by setting the length LT in this manner. In addition, it is necessary to select values for LB and $\theta o$ that satisfy the condition LB>Lb1 such that the excitation light beam is not irradiated onto the corner between the lower surface and the light output surface of the prism 110. Here, Lb1 is expressed by the following formula.

$$Lb1 = H/\tan\{(\pi/2) - (\phi - \psi)\} - (D - Db)$$

Therefore, the value of Db is derived. In order to derive the value of Db, the coordinates (x4', y4') of the point at which the excitation light beam 146B intersects with the prism 110 are obtained in the same manner as for Da. x4' and y4' are expressed by the following formulas.

$$x4' = \tan\{(\pi/2) - \phi\}[F - (D - x1)/\cos\{(\pi/2) - \phi\}]/\tan(-\psi) + \tan\{(\pi/2) - \phi\}]$$

$$y4'=-\tan(-\psi)\cdot\tan\{(\pi/2)-\phi\}[F-(D-x1)/\cos\{(\pi/2)-\phi\}]/\{\tan(-\psi)+\tan\{(\pi/2)-\phi\}\}$$

Accordingly, Db can be expressed by the following formula.

$$Db=\sqrt{\{(x4'-x2')^2+y4'-y2'^2\}}$$

Figure 12:
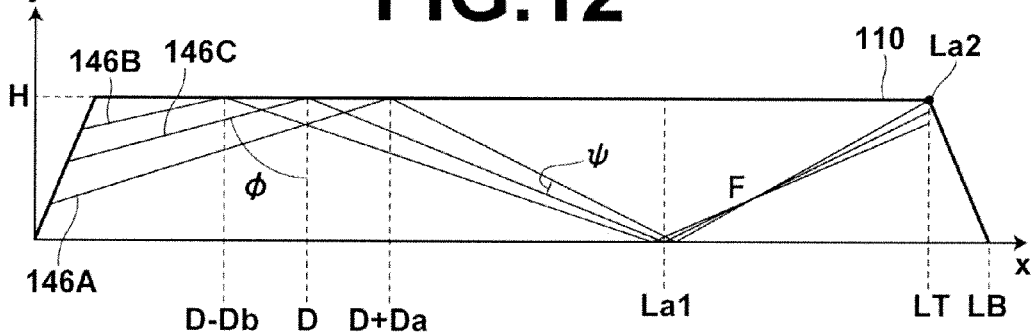
FIG. 12 is a diagram that illustrates a case in which an excitation light beam is reflected twice within a prism, and a focal point is positioned following the second reflection.

Finally, a case in which the focal point F is present following La1 as illustrated in FIG. 12 will be considered. In this case, the excitation light beam 146A will not be irradiated onto the corner formed by the upper surface and the light output surface of the prism 110 as long as LT<La2, as in the case described with reference to FIG. 11. In addition, the excitation light beam 146A will not be irradiated onto the coiner formed by the lower surface and the light output surface of the prism 110 as long as LB>La1. Returning light will not be generated by setting LB and LT in this manner.

By setting the shape of the prism 110 as described above, the excitation light beam is not irradiated onto the corners of the light output surface of the prism 110. Therefore, returning light is eliminated, light emission by the light source section is stabilized, and the accuracy of measurement is improved.

Figure 13:
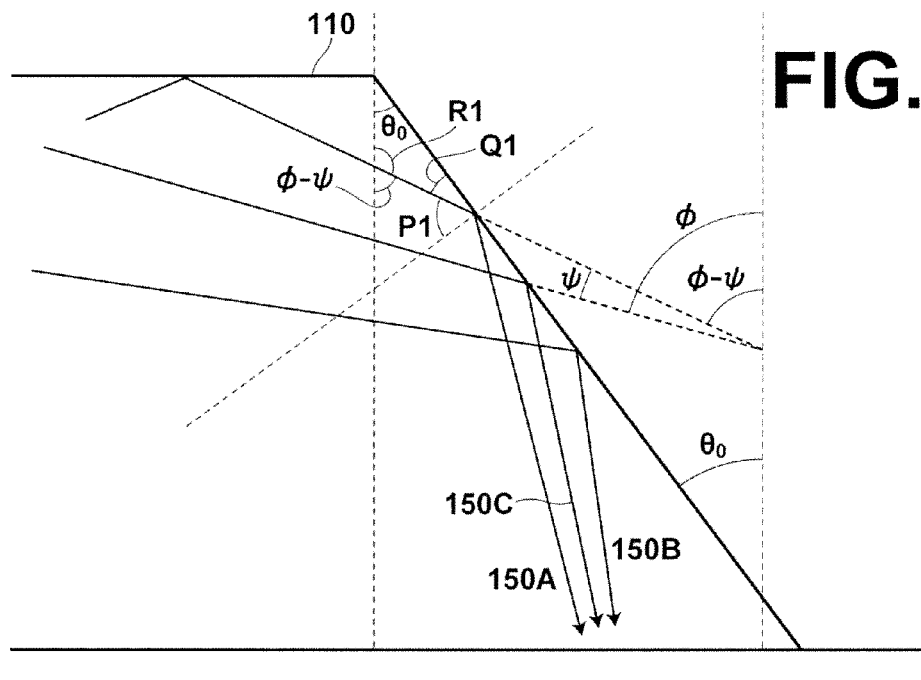
FIG. 13 is a magnified diagram of a light output surface of a prism for a case in which an excitation light beam is reflected once within a prism, and then exits the prism.

Next, conditions with respect to the angle θo formed by the light output surface and the y axis that will prevent the excitation light beam from being totally reflected will be considered. FIG. 13 is a diagram that illustrates a case in which a single reflection occurs within the prism and θo>0. In this case, an excitation light beam 150A is incident onto the light output surface at the greatest incident angle P1. Angle R1 is derived in order to derive the incident angle P1.

$$R1=\pi-\phi+\psi$$

Then, R1 and θo are employed to derive Q1.

$$Q1=\pi-(\theta o+R1)$$

Accordingly, P1 can be derived by the following formula.

$$P1=(\pi/2)-Q1=-\phi+\psi+\theta o+(\pi/2)$$

The excitation light beam will not be totally reflected at the light output surface if this angle is less than a total reflection angle θc. The conditions with respect to the angle θo that will prevent the excitation light beam from being totally reflected are expressed by the following formula.

$$\theta o<\phi-\psi+\theta c-\pi/2$$

Figure 14A:
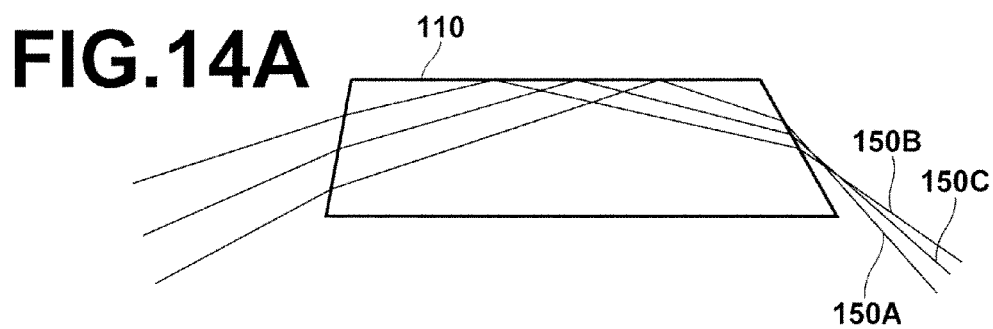
FIG. 14A is a diagram that illustrates a case in which the excitation light beam of FIG. 13 is not totally reflected at the light output surface.
Figure 14B:
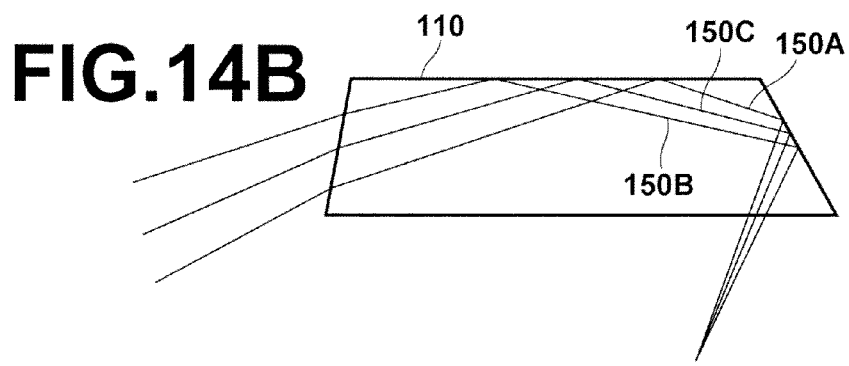
FIG. 14B is a diagram that illustrates a case in which the excitation light beam of FIG. 13 is totally reflected at the light output surface.

If θo is less than $\phi-\psi+\theta c-\pi/2$, substantially all of the excitation light beam will be output from the prism 110, as illustrated in FIG. 14A. If θo is greater than or equal to $\phi-\psi+\theta c-\pi/2$, the excitation light beam will be totally reflected at the light output surface as illustrated in FIG. 14B, return to the interior of the prism, and will become factors that cause unnecessary scattered light.

Figure 15:
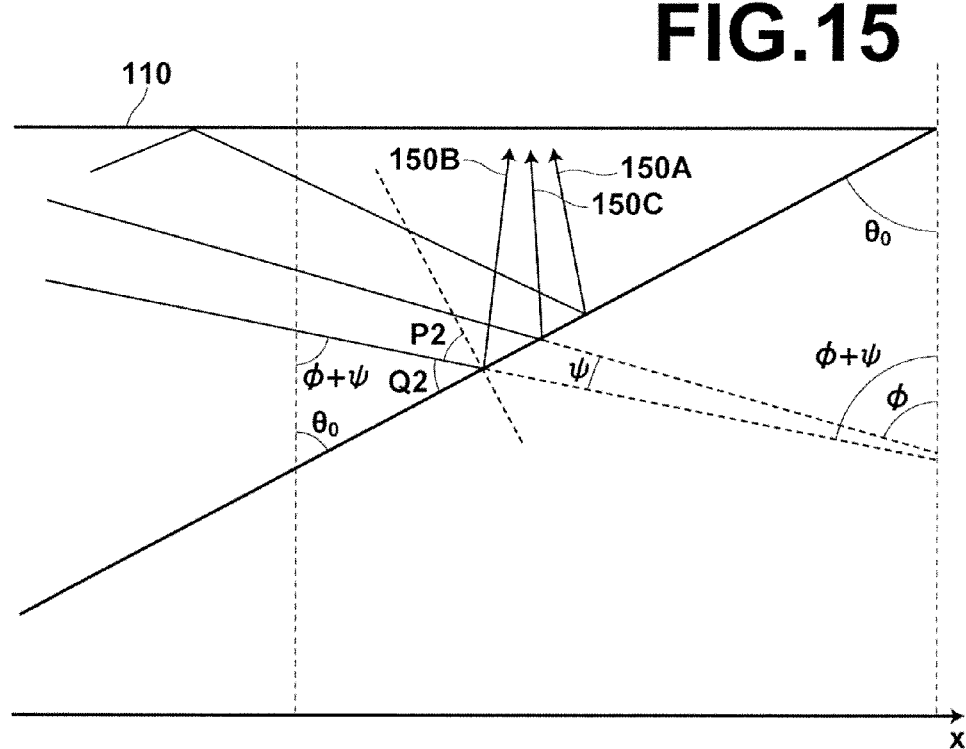
FIG. 15 is a magnified diagram of a light output surface of a prism for a case in which an excitation light beam is reflected once within a prism, and then exits the prism.

FIG. 15 is a diagram that illustrates a case in which an excitation light beam is reflected once within a prism, and θo<0. In this case, the excitation light beam 150B is incident onto the light output surface at the greatest incident angle P2. Q2 of FIG. 15 is expressed by the following formula.

$$Q2=\pi-|\theta o|-\phi-\psi$$

Therefore, the incident angle P2 at which the excitation light beam 150B is incident on the light output surface is expressed by the following formula.

$$P2=(\pi/2)-Q2=\phi+\psi+|\theta o|-(\pi/2)$$

The excitation light beam will not be totally reflected at the light output surface if this angle is greater than a total reflection angle θc. The conditions with respect to the angle θo that will prevent the excitation light beam from being totally reflected are expressed by the following formula.

$$\theta o>\phi+\psi-\theta c-(\pi/2)$$

Figure 16A:
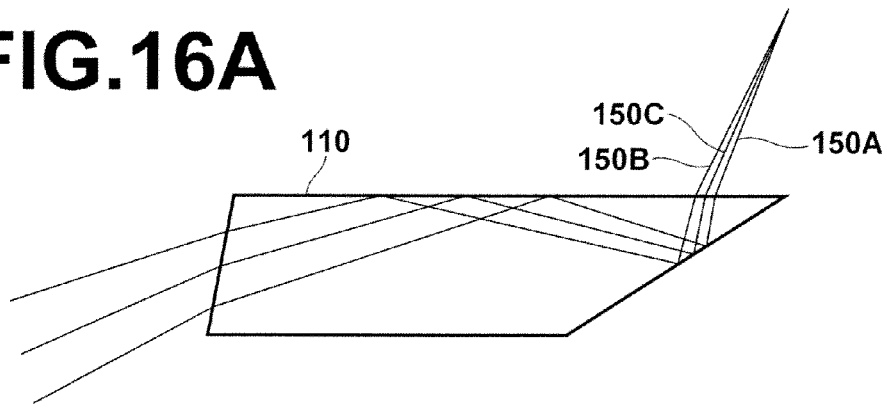
FIG. 16A is a diagram that illustrates a case in which the excitation light beam of FIG. 15 is totally reflected at the light output surface.
Figure 16B:
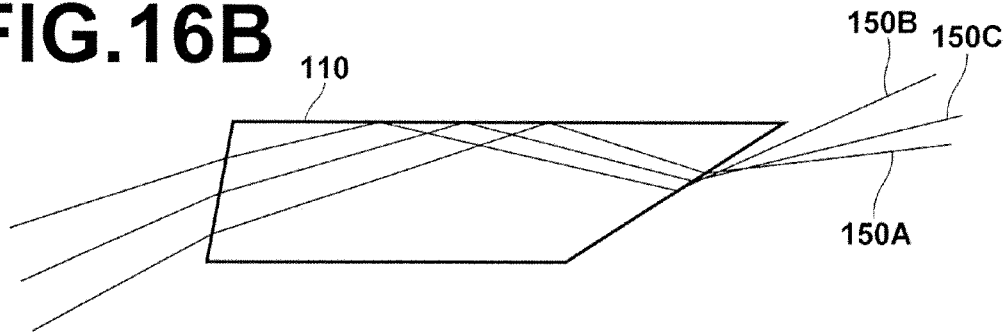
FIG. 16B is a diagram that illustrates a case in which the excitation light beam of FIG. 15 is not totally reflected at the light output surface.

If θo is less than or equal to $\phi+\psi-\theta c-(\pi/2)$, the excitation light beam will be totally reflected at the light output surface as illustrated in FIG. 16A, return to the interior of the prism, and will become factors that cause unnecessary scattered light. If θo is greater than $\phi+\psi-\theta c-\pi/2$, substantially all of the excitation light beam will be output from the prism 110, as illustrated in FIG. 16B.

As described above, in the case that an excitation light beam is reflected once within the prism, the excitation light beam can be prevented from being totally reflected at the light output surface of the prism 110 by setting θo to satisfy the following condition.

$$\phi+\psi-\theta c-(\pi/2)<\theta o<\phi-\psi+\theta c-(\pi/2)$$

For example if φ is 75 degrees, ψ is 0 degrees, and the refractive index of the prism 110 is 1.49, the critical angle θc will be 42.16 degrees. Accordingly, the excitation light beam can be prevented from being totally reflected at the light output surface of the prism 110 by setting the value of θo to satisfy the following condition.

$$-57.16<\theta o<27.16$$

Figure 17:
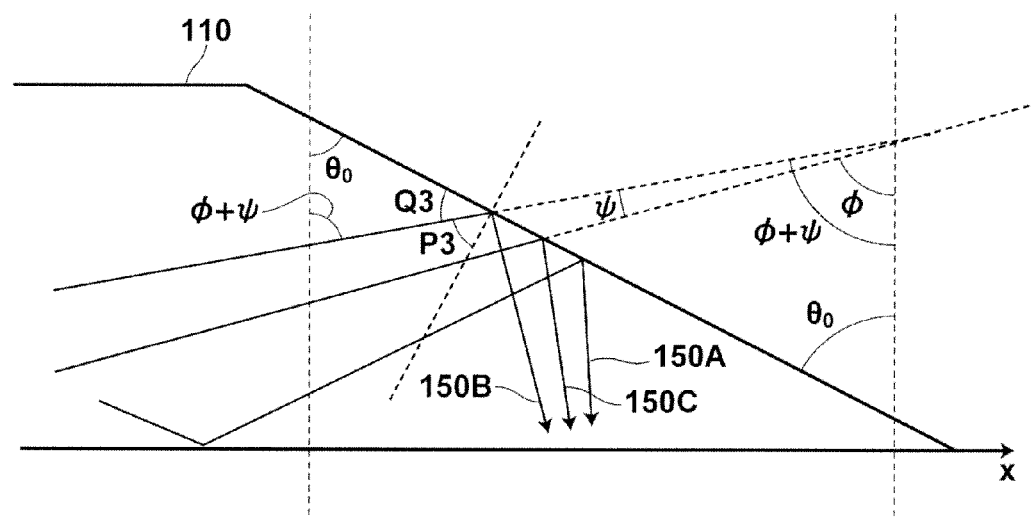
FIG. 17 is a magnified diagram of a light output surface of a prism for a case in which an excitation light beam is reflected twice within a prism, and then exits the prism.

Next, a case in which an excitation light beam is reflected twice within the prism 110 will be considered. FIG. 17 is a diagram that illustrates a case in which reflection occurs twice within the prism and θo>0. In this case, the excitation light beam 150B is incident onto the light output surface at the greatest incident angle P3. Q3 of FIG. 17 is expressed by the following formula.

$$Q3=\pi-\theta o-\phi-\psi$$

Therefore, the incident angle P3 at which the excitation light beam 150B is incident on the light output surface is expressed by the following formula.

$$P3=(\pi/2)-Q3=-(\pi/2)+\phi+\psi+\theta o$$

The excitation light beam will not be totally reflected at the light output surface if this angle is less than a total reflection angle θc. The conditions with respect to the angle θo that will prevent the excitation light beam from being totally reflected are expressed by the following formula.

$$\theta o<(\pi/2)-\phi-\psi+\theta c$$

Figure 18A:
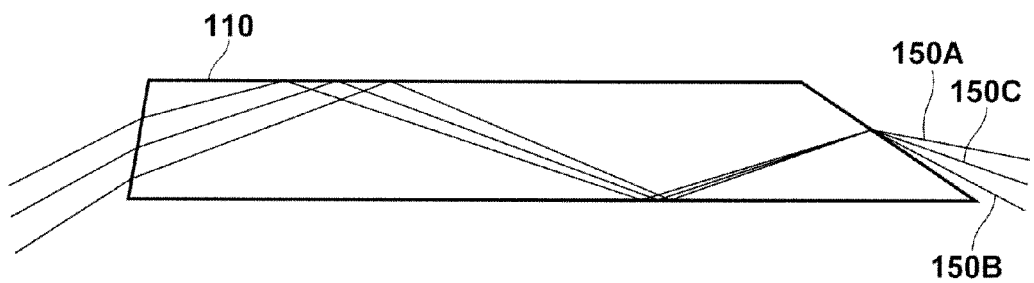
FIG. 18A is a diagram that illustrates a case in which the excitation light beam of FIG. 17 is not totally reflected at the light output surface.
Figure 18B:
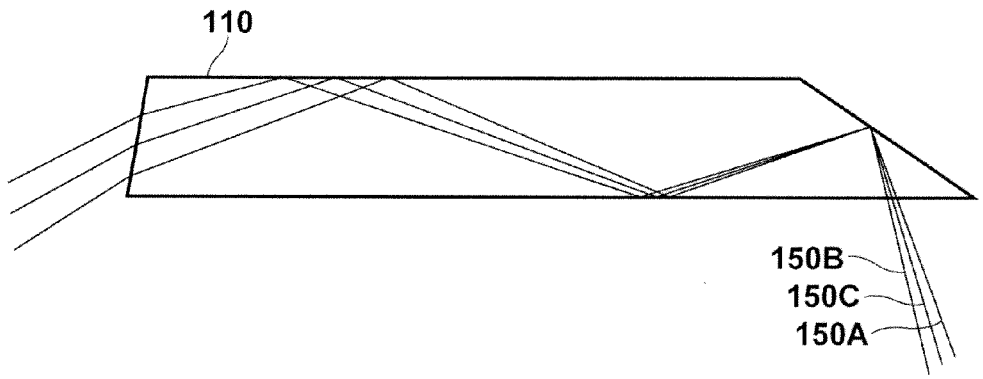
FIG. 18B is a diagram that illustrates a case in which the excitation light beam of FIG. 17 is totally reflected at the light output surface.

If θo is less than $(\pi/2)-\phi-\psi+\theta c$, substantially all of the excitation light beam will be output from the prism 110, as illustrated in FIG. 18A. If θo is greater than or equal to $(\pi/2)-\phi-\psi+\theta c$, the excitation light beam will be totally reflected at the light output surface as illustrated in FIG. 18B, return to the interior of the prism, and will become factors that cause unnecessary scattered light.

Figure 19:
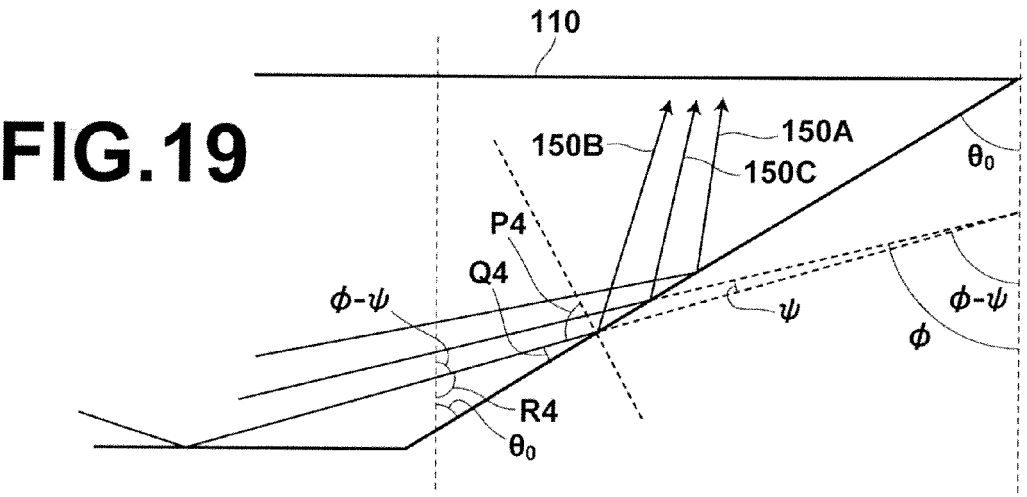
FIG. 19 is a magnified diagram of a light output surface of a prism for a case in which an excitation light beam is reflected twice within a prism, and then exits the prism.

FIG. 19 is a diagram that illustrates a case in which reflection occurs twice within the prism and θo<0. In this case, the excitation light beam 150A is incident onto the light output surface at the greatest incident angle P4. R4 of FIG. 19 is expressed by the following formula.

$$R4=\pi-\phi+\psi$$

Q4 of FIG. 19 is expressed by the following formula.

$$Q4=\pi-R4-|\theta o|$$

Therefore, the incident angle P4 at which the excitation light beam 150A is incident on the light output surface is expressed by the following formula.

$$P4=(\pi/2)-Q4=-(\pi/2)+\phi-\psi-|\theta o|$$

The excitation light beam will not be totally reflected at the light output surface if this angle is greater than a total reflection angle θc. The conditions with respect to the angle θo that will prevent the excitation light beam from being totally reflected are expressed by the following formula.

$$\theta o > (\pi/2) - \phi + \psi - \theta c$$

Figure 20A:
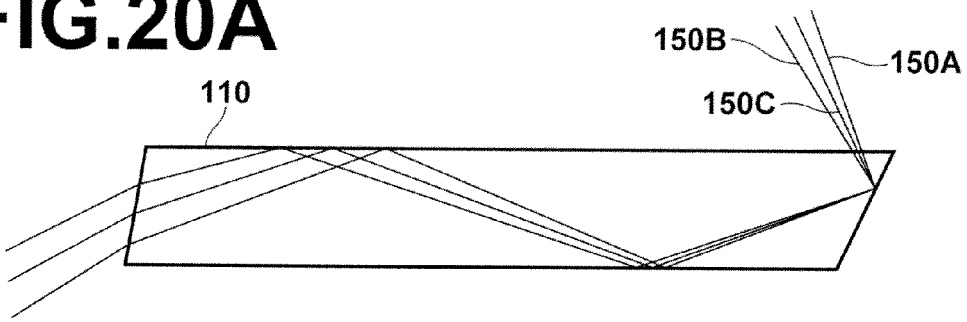
FIG. 20A is a diagram that illustrates a case in which the excitation light beam of FIG. 19 is totally reflected at the light output surface.
Figure 20B:
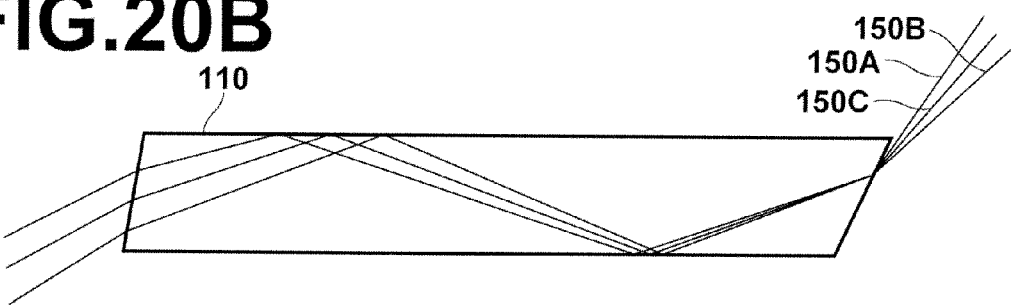
FIG. 20B is a diagram that illustrates a case in which the excitation light beam of FIG. 19 is not totally reflected at the light output surface.

If θ0 is less than or equal to $(\pi/2)-\phi+\psi-\theta c$, the excitation light beam will be totally reflected at the light output surface as illustrated in FIG. 20A, return to the interior of the prism, and will become factors that cause unnecessary scattered light. If θo is greater than $(\pi/2)-\phi+\psi-\theta c$, substantially all of the excitation light beam will be output from the prism 110, as illustrated in FIG. 20B.

As described above, in the case that an excitation light beam is reflected twice within the prism, the excitation light beam can be prevented from being totally reflected at the light output surface of the prism 110 by setting θo to satisfy the following condition.

$$(\pi/2)-\phi+\psi-\theta c < \theta o < (\pi/2)-\phi-\psi+\theta c$$

For example if ϕ is 75 degrees, ψ is 0 degrees, and the refractive index of the prism 110 is 1.49, the critical angle θc will be 42.16 degrees. Accordingly, the excitation light beam can be prevented from being totally reflected at the light output surface of the prism 110 by setting the value of θo to satisfy the following condition.

$$-27.16 < \theta o < 57.16$$

With respect to the angle formed by the excitation light beam and the light output surface, in the case that $(\phi \pm \psi) - \theta o$ for an odd number of internal reflections, and $\pi - (\phi \pm \psi) - \theta o$ for an even number of internal reflections equals π/2, the excitation light beam is. incident onto the light output surface perpendicularly. That is, such an angle will result in regular reflection, which is equivalent to the excitation light beam being irradiated onto a corner of the prism, and returning light that returns to the light source will be generated. Therefore in the case of an odd number of internal reflections, it is necessary to avoid angles θo within a range defined by the conditions below, in addition to the conditions described above.

$$(\phi-\psi)-\pi/2 < \theta o < (\phi+\psi)-\pi/2$$

Likewise, in the case of an even number of internal reflections, it is necessary to avoid angles θo within a range defined by the conditions below, in addition to the conditions described above.

$$\pi/2-(\phi+\psi) < \theta o < \pi/2-(\phi-\psi)$$

It is desirable for the angle θo with respect to the central optical axis 146C of the excitation light beam to be a Brewster angle. If θo is set to a Brewster angle, reflection of the excitation light beam at the interface between the prism 110 and the exterior is further reduced, and the accuracy of measurement is improved.

Note that the vicinity of the point at which the excitation light beam is reflected the second time may be formed as a scattering surface. If the scattering surface is provided in the vicinity of the point at which the excitation light beam is reflected the second time, the excitation light beam is scattered and regularly reflected returning light components are relatively reduced. Therefore, similar advantageous effects as those obtained by not causing the excitation light beam to be irradiated onto the corners of the prism.

In addition, the first embodiment was described for cases in which the excitation light beam is reflected once and twice. However, the number of reflections is not limited to one and two. In the case of an odd number of reflections, the same calculations as those employed for one reflection are applied, and in the case of an even number of reflections, the same calculations as those employed for two reflections are applied.

Second Embodiment

Figure 21:
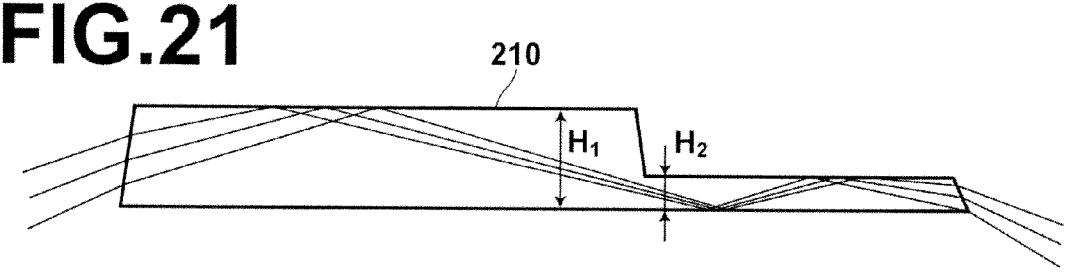
FIG. 21 is a diagram that illustrates the shape of an optical member according to a second embodiment of the present invention.

FIG. 21 is a diagram that illustrates the sectional shape of a prism 210 according to a second embodiment of the present invention. The prism 210 is the same as the prism 110 of the first embodiment except for the shape thereof. The height of the prism 210 changes along the propagating direction of light. If the height of the prism 210 at the portion near the light incident surface is designated as H1, and the height of the prism 210 at the portion near the light output surface is designated as 112, the heights satisfy the condition H1>H2. That is, the height of the prism 210 is formed to have two steps, and the height near the light output surface is lower. Even if the height of the prism 210 is changed in this manner, if the shape thereof is set by changing the value of H of the formulas described with respect to the first embodiment, the shape of the prism 210 can be set such to that which eliminates the occurrence of returning light.

If the shape of the prism 210 is set as in the second embodiment, the prism 210, in which an excitation light beam is not irradiated onto the corners of the prism can be obtained even for cases that it is desired to narrow the width of the excitation light beam to be output from the prism.

As described above, the present invention sets the shape of a prism such that an excitation light beam is not irradiated onto the corners of the prism. The angle of the light output surface is set such that the excitation light beam is not totally reflected or regularly reflected at the light output surface. Therefore, returning light is not generated, and the excitation light is not totally reflected or regularly reflected at the light output surface, resulting in improved measurement accuracy.

What is claimed is:

1. A surface plasmon resonance measuring apparatus equipped with an optical member comprising a metal film, into which an excitation light beam enters at surface plasmon resonance angles and generates surface plasmon by being totally reflected by the metal film, the optical member comprising:

an upper surface which is in contact with the metal film;
a lower surface that faces the upper surface;
a light incident surface connected to the upper surface and the lower surface, through which the excitation light beam enters the optical member; and
a light output surface connected to the upper surface and the lower surface, through which the excitation light beam is output,
wherein a distance between the light incident surface and the light output surface, and an angle formed by axes perpendicular to the light output surface and a bottom surface of the optical member are defined such that the excitation light beam enters the light incident surface at a plurality of different angles with respect to the metal film that satisfy the surface plasmon resonance angles, is totally reflected by the metal film, is not reflected by a corner between the upper surface and the light output surface, by a corner between the lower surface and the light output surface, and by the light output surface.

2. The surface plasmon resonance measuring apparatus as defined in claim 1, wherein an angle of the light output surface of the optical member is set such that an angle of the excitation light beam with respect to the light output surface and an axis perpendicular to the lower surface is smaller than an angle at which the excitation light beam is totally reflected.

3. The surface plasmon resonance measuring apparatus as defined in claim 2, wherein the angle of the light output surface of the optical member is set such that the angle of the excitation light beam with respect to the light output surface comprises a Brewster angle.

4. The surface plasmon resonance measuring apparatus as defined in claim 1, wherein the optical member is provided with a scattering surface at a position at which the excitation light beam that enters the metal film at the surface plasmon resonance angles that is totally reflected by the metal film is totally reflected at the lower surface.

5. The surface plasmon resonance measuring apparatus as defined in claim 1, wherein a portion of the reflected excitation light enters corners of the optical member.

6. The surface plasmon resonance measuring apparatus as defined in claim 1, wherein the optical member comprises a scattering surface at a position at which the excitation light beam is totally reflected at the lower surface.

7. The surface plasmon resonance measuring apparatus as defined in claim 6, wherein the scattering surface is provided in a vicinity of a point at which the excitation light beam is reflected.

* * * * *